United States Patent
Comaniciu et al.

(10) Patent No.: US 9,462,952 B2
(45) Date of Patent: Oct. 11, 2016

(54) SYSTEM AND METHOD FOR ESTIMATING ARTERY COMPLIANCE AND RESISTANCE FROM 4D CARDIAC IMAGES AND PRESSURE MEASUREMENTS

(71) Applicants: Dorin Comaniciu, Princeton Junction, NJ (US); Bogdan Georgescu, Plainsboro, NJ (US); Ali Kamen, Skillman, NJ (US); Tommaso Mansi, Plainsboro, NJ (US); Viorel Mihalef, North Brunswick, NJ (US)

(72) Inventors: Dorin Comaniciu, Princeton Junction, NJ (US); Bogdan Georgescu, Plainsboro, NJ (US); Ali Kamen, Skillman, NJ (US); Tommaso Mansi, Plainsboro, NJ (US); Viorel Mihalef, North Brunswick, NJ (US)

(73) Assignee: Siemens Aktiengesellschaft, Munich (DE)

( * ) Notice: Subject to any disclaimer, the term of this patent is extended or adjusted under 35 U.S.C. 154(b) by 201 days.

(21) Appl. No.: 14/455,500

(22) Filed: Aug. 8, 2014

(65) Prior Publication Data
US 2015/0045644 A1 Feb. 12, 2015

Related U.S. Application Data

(60) Provisional application No. 61/864,199, filed on Aug. 9, 2013.

(51) Int. Cl.
| | | |
|---|---|---|
| A61B 5/02 | (2006.01) |
| A61B 5/026 | (2006.01) |
| A61B 8/04 | (2006.01) |
| A61B 5/00 | (2006.01) |
| A61B 8/08 | (2006.01) |
| A61B 6/03 | (2006.01) |
| A61B 6/00 | (2006.01) |
| A61B 5/029 | (2006.01) |
| A61B 5/021 | (2006.01) |
| A61B 8/06 | (2006.01) |
| G06T 7/00 | (2006.01) |
| A61B 5/055 | (2006.01) |

(52) U.S. Cl.
CPC .......... *A61B 5/02007* (2013.01); *A61B 5/029* (2013.01); *A61B 5/0263* (2013.01); *A61B 6/503* (2013.01); *A61B 6/5217* (2013.01); *G06T 7/0016* (2013.01); *G06T 7/0081* (2013.01); *A61B 5/0037* (2013.01); *A61B 5/0044* (2013.01); *A61B 5/02125* (2013.01); *A61B 5/055* (2013.01); *A61B 8/065* (2013.01); *G06T 2207/30101* (2013.01); *G06T 2207/30104* (2013.01)

(58) Field of Classification Search
CPC .............. A61B 5/0037; A61B 5/0044; A61B 5/02007; A61B 5/02125; A61B 5/0263; A61B 5/029; A61B 5/055; A61B 6/503; A61B 6/5217; A61B 8/065; G06T 2207/30101; G06T 2207/30104; G06T 7/0016; G06T 7/0081
See application file for complete search history.

(56) References Cited

U.S. PATENT DOCUMENTS

| | | |
|---|---|---|
| 7,916,919 B2 | 3/2011 | Zheng et al. |
| 8,098,918 B2 | 1/2012 | Zheng et al. |

(Continued)

*Primary Examiner* — Michael Rozanski

(57) ABSTRACT

A method and system for estimating arterial compliance and resistance based on medical image data and pressure measurements is disclosed. An arterial inflow estimate over a plurality of time points is determined based on medical image data of a patient. An arterial pressure measurement of the patient is received. At least one cardiac cycle of the arterial pressure measurement is synchronized with at least one cardiac cycle of the arterial inflow measurement. Arterial compliance and resistance of the patient is estimated based on the arterial inflow estimate and the synchronized arterial pressure measurement.

28 Claims, 7 Drawing Sheets

(56) References Cited

U.S. PATENT DOCUMENTS

| | | |
|---|---|---|
| 8,282,564 B2 | 10/2012 | Parlikar et al. |
| 8,406,496 B2 | 3/2013 | Zheng et al. |
| 8,682,626 B2 | 3/2014 | Ionasec et al. |
| 2008/0287812 A1 | 11/2008 | Parlikar et al. |
| 2012/0078097 A1 | 3/2012 | Wang et al. |
| 2013/0006127 A1 | 1/2013 | Parlikar et al. |
| 2014/0135634 A1 | 5/2014 | Pranevicius et al. |
| 2014/0303509 A1 | 10/2014 | Campbell |

SYSTEM AND METHOD FOR ESTIMATING ARTERY COMPLIANCE AND RESISTANCE FROM 4D CARDIAC IMAGES AND PRESSURE MEASUREMENTS

This application claims the benefit of U.S. Provisional Application No. 61/864,199, filed Aug. 9, 2013, the disclosure of which is herein incorporated by reference in its entirety.

BACKGROUND OF THE INVENTION

The present invention relates to estimating arterial parameters of a patient based on medical image data and clinical measurements, and more particularly, to estimating arterial compliance and resistance from 4D cardiac images and pressure measurements.

Estimation of artery compliance and resistance can provide key information on the systemic pulmonic resistance of a patient. From a clinical point of view, artery resistance parameters can be used to quantify hypertension effects on heart failure. Hypertension is a risk factor for the development of heart failure, as it increases cardiac work, thus leading to the development of left ventricular hypertrophy. Consequently, it is desirable to lower systemic vascular resistance in order to reduce blood pressure in both the population affected by heart failure and the normal population.

In current clinical practice, the parameters of arterial compliance and resistance are typically estimated invasively based on invasive pressure measurements acquired during cardiac catheterization using an empirical law. More sophisticated methods for estimating these parameters based on inverse modeling have also been proposed. However, such methods require measurements of blood flow and pressure to be acquired simultaneously, which is difficult to achieve.

BRIEF SUMMARY OF THE INVENTION

The present invention provides a method and system for estimating artery compliance and resistance of a patient based on medical image data and pressure measurements. Embodiments of the present invention provide a method and system for estimating arterial compliance and resistance from pressure measurements and image-based blood flow measurements that are not acquired simultaneously. Embodiments of the present invention utilize a heart rate adjustment procedure to synchronize flow and pressure in time while respecting patient-specific cardiac physiology, and then employ inverse modeling to estimate arterial compliance and resistance.

In one embodiment of the present invention, an arterial inflow estimate over a plurality of time points is determined based on medical image data of a patient. An arterial pressure measurement of the patient is received. At least one cardiac cycle of the arterial pressure measurement is synchronized with at least one cardiac cycle of the arterial inflow measurement. Arterial compliance and resistance of the patient is estimated based on the arterial inflow estimate and the synchronized arterial pressure measurement.

These and other advantages of the invention will be apparent to those of ordinary skill in the art by reference to the following detailed description and the accompanying drawings.

DETAILED DESCRIPTION

Figure 1:
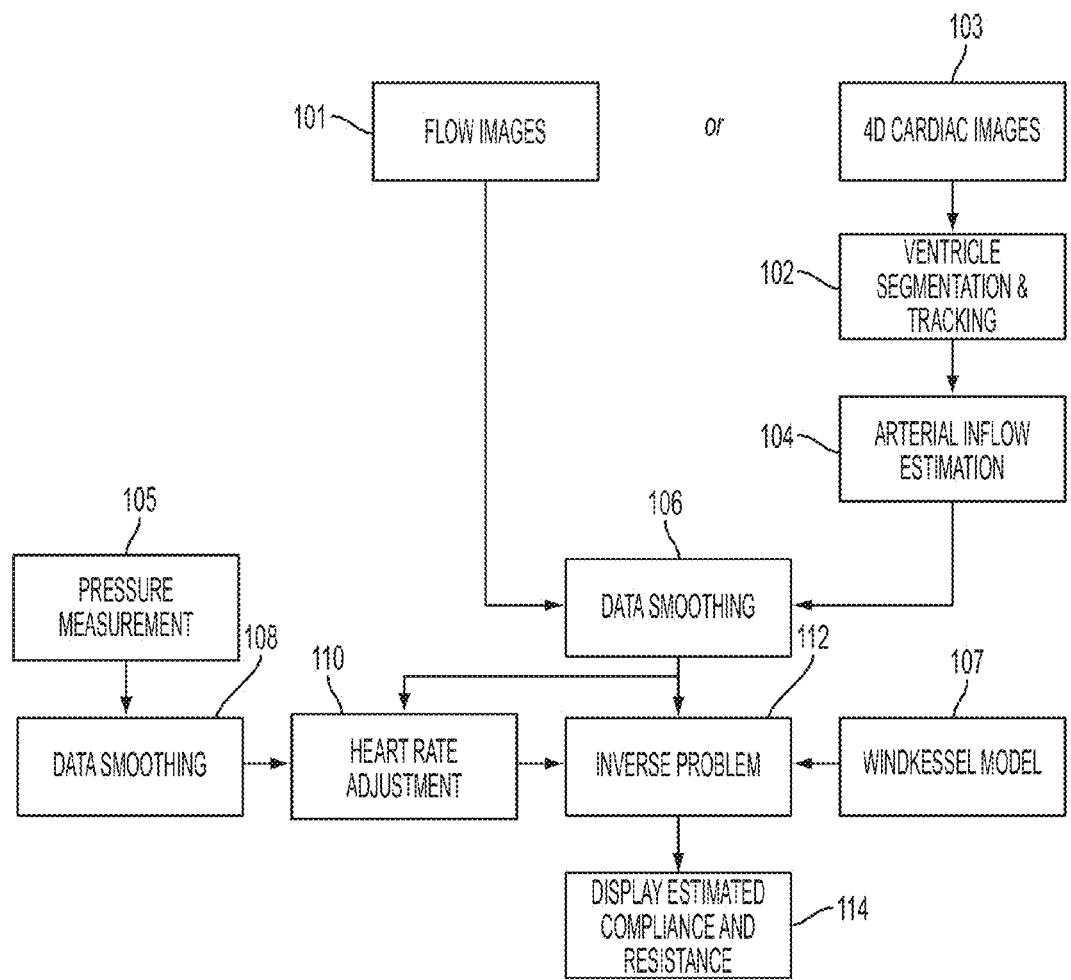
FIG. 1 illustrates a framework for estimating arterial compliance and resistance of a patient according to an exemplary embodiment of the present invention.

The present invention relates to estimating arterial compliance and resistance from medical image data and pressure measurements. Embodiments of the present invention are described herein to give a visual understanding of the methods for estimating arterial compliance and resistance using medical imaging data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Patient-specific artery boundary conditions are important for accurate blood flow computation and cardiac stiffness estimation through inverse problem solving. An inverse problem (IP) framework can be used for estimating physiological parameters, including vessel, systematic, or cardiac compliance and resistance. The basic idea of the IP framework is to estimate, in a first step, the space generated by parameter varying for parameterized forward simulations that model the cardiovascular interaction between flow, pressure, and elastic walls. In a second step, a best parametric fit is determined given the available measured quantities. One limitation of using the IP framework for estimating the arterial compliance and resistance is that the IP framework typically relies on flow and pressure data that are acquired simultaneously. This is not usually the case for clinical data. Embodiments of the present invention provide a method and system for estimating arterial compliance and resistance even in cases in which the pressure measurements and the medical image data from which the flow is determined are not acquired simultaneously.

Embodiments of the present invention combine advanced image analytics, inverse problem modeling, and a physiologically-consistent method for temporal synchronization of pressure and flow data to estimate arterial compliance and resistance from medical image data and clinical pressure measurements. Embodiments of the present invention address issues of data synchrony and flow availability by synchronizing pressure and flow datasets using a physiologically consistent synchronization method and using machine learning algorithms to automatically segmented the cardiac chambers over time on 4D cardiac images. Embodiments of the present invention utilize a Windkessel model of blood vessels to estimate artery compliance and resistance. The resulting parameters can be displayed and provided to the user as additional biomarkers for disease assessment. The estimated arterial parameters (compliance, resistance, remote pressure) can be provided to a clinician for diagnostic purposes to help the clinician make decisions regarding disease diagnosis and treatment options. The estimated arterial parameters may also be used in more complex models, such as computational fluid dynamics or whole-heart modeling, for advanced physiological measurements or therapy planning (e.g., model-based prediction of cardiac resynchronization therapy).

FIG. 1 illustrates a framework for estimating arterial compliance and resistance of a patient according to an exemplary embodiment of the present invention. In the exemplary embodiment of FIG. 1, arterial inflow (i.e., blood flow at the exit of the ventricle) can be acquired using medical images that provide flow information ("Flow images" 101), such as 2D phase contrast magnetic resonance imaging (PCMRI) or Doppler ultrasound. When these images are not available for a patient, 4D cardiac images (103) are acquired (e.g., cine MRI, ultrasound B-mode, computed tomography (CT)) and machine learning algorithms are used to automatically segment chambers of the heart throughout the cardiac image sequence ("Ventricle Segmentation Tracking" 102). The resulting mesh is then used to estimate the blood pool volume and blood flow through the artery ("Arterial inflow estimation" 104). Arterial and venous pressure measurements (105) of the patient are acquired, and after smoothing the flow data (106) and the pressure data (108), a heart rate adjustment procedure (110) is used to synchronize the flow and pressure measurements of the patient in time while respecting cardiac physiology. Inverse problem modeling (112) is then employed to estimate the arterial compliance and resistance by optimizing parameters of a Windkessel model (107) representing the artery based on the synchronized pressure and flow data. The estimated arterial compliance and resistance can then be output by displaying the estimated arterial compliance and resistance on a display of a computer system (114). It is to be understood that FIG. 1 provides and exemplary embodiment and the elements of FIG. 1 are described in greater detail in the description of the methods of FIGS. 2 and 5 below.

Figure 2:
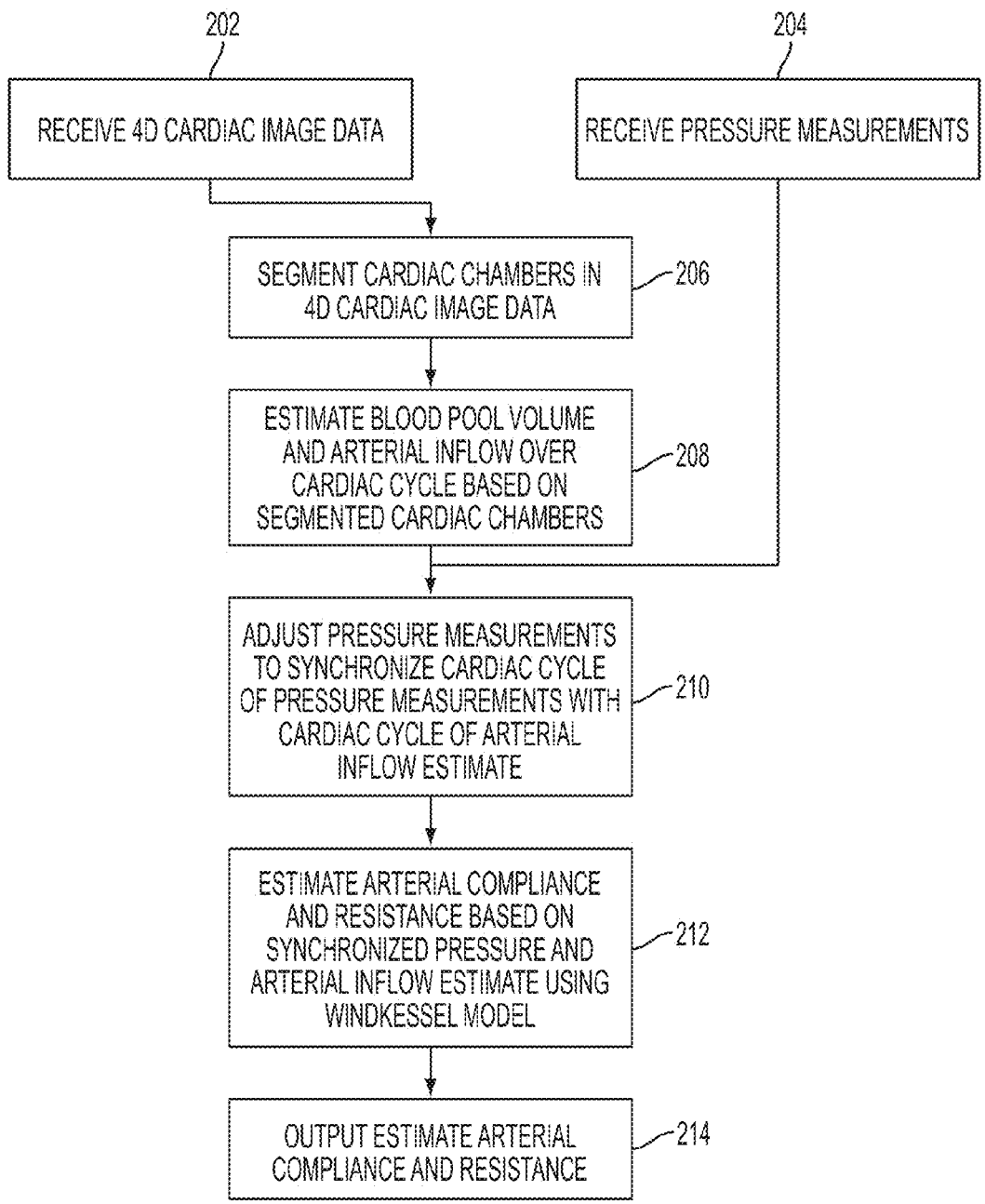
FIG. 2 illustrates a method for estimating arterial compliance and resistance according to an embodiment of the present invention.

FIG. 2 illustrates a method for estimating arterial compliance and resistance according to an embodiment of the present invention. Referring to FIG. 2, at step 202, 4D cardiac image data of a patient is received. The 4D cardiac image data is a sequence of 3D cardiac images acquired over at least one heart cycle. The 4D cardiac image data can be acquired using any type of medical imaging modality, such as computed tomography (CT), three-dimensional rotational angiography, magnetic resonance imaging (MRI), ultrasound (US), etc., provided that the heart is entirely visible in the medical image data. The 4D cardiac image data can be received directly from an image acquisition device, such as a CT scanner, a C-arm image-acquisition device, an MRI scanner, or an US scanner, or the pre-operative cardiac image data can be received by loading previously stored cardiac image data of the patient. In addition or as an alternative to the 4D cardiac image data, medical images that provide blood flow information, such as 2D phase contrast magnetic resonance imaging (PCMRI) or Doppler ultrasound, can also be received and used to measure the blood flow of the patient.

At step 204, a pressure measurement of the patient is received. The pressure measurement is a measurement of arterial blood pressure and may also include a measurement of ventricular blood pressure measurements of the patient over one or more cardiac cycles are received. In an advantageous embodiment, the pressure measurement may be acquired invasively via a pressure wire during cardiac catheterization. Alternatively, the pressure measurement can be acquired non-invasively, for example by measuring the radial arterial pulse pressure. In another possible embodiment, in a case in which no invasive pressure measurement is available but 4D flow images (e.g., PC-MRI) are available, a pressure field can be estimated at the arterial root from the 4D flow images using physics based computation methods, such as computational fluid dynamics. It is to be understood that the blood pressure measurement can be acquired at a separate time as the 4D cardiac images and the acquisition of the blood pressure measurement does not need to be synchronized with the acquisition of the 4D cardiac images.

Figure 3:
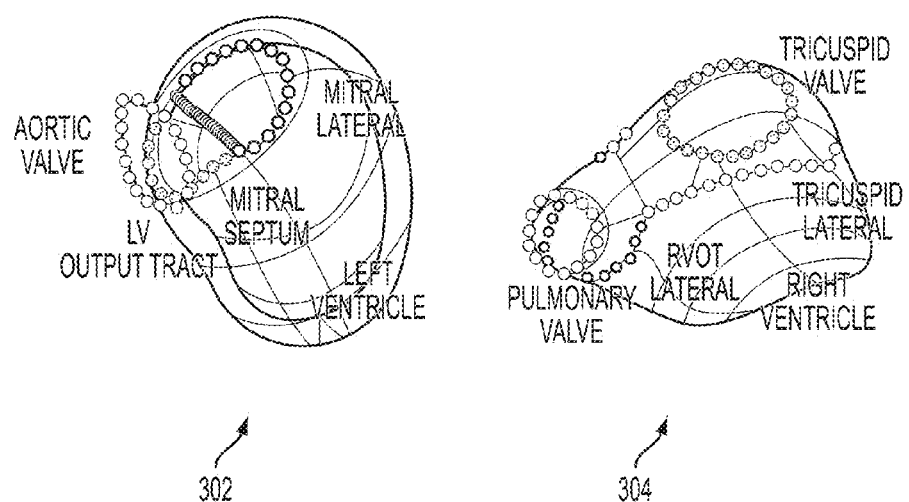
FIG. 3 illustrates exemplary models of the left and right ventricle.

At step 206, the cardiac chambers are segmented in the 4D cardiac image data. In particular, the cardiac chambers are segmented in each frame of the 4D image data. According to an advantageous embodiment, the segmentation of the cardiac chambers leverages comprehensive heart models learned from a database of training data. Such heart models are described in greater detail in U.S. Pat. No. 7,916,919, U.S. Pat. No. 8,682,626, and U.S. Pat. No. 8,406,496, the disclosures of which are incorporated herein by reference. Physiological landmarks are explicitly encoded in the models and provide semantic associations with the underlying anatomy. The models are highly modular and can be customized depending on the application. According to an advantageous implementation, the left and right ventricles are segmented. FIG. 3 illustrates exemplary models of the left and right ventricle. As illustrated in FIG. 3, the left ventricle model 300 and the right ventricle model 302 provide explicitly geometrical representations for the left ventricle endocardium, epicardium, mitral annulus, left ventricular outflow tract, ventricular regions, and tricuspid and pulmonary valve locations.

The models can be personalized given any imaging modality (CT, MR, Ultrasound, etc.) and the model parameters can be automatically determined from the imaging data data-based guided machine-learning based segmentation. The model for each cardiac chamber can be extracted individually in each frame of the 4D cardiac image data. In particular, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object learned from a database of training data is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916, 919, issued Mar. 29, 2011, and entitled "System and Method for Segmenting Chambers of a Heart in a Three Dimensional Image", U.S. Pat. No. 8,406,496, and U.S. Pat. No. 8,682, 626, which are incorporated herein by reference. According to a possible implementation, motion manifold learning can also be used for estimating temporal components and dynamics of the heart models derived explicitly from the patient scans. Motion manifold learning is described in greater detail in United States Published Patent Application No. 2012/0078097, which is incorporated herein by reference.

Figure 4:
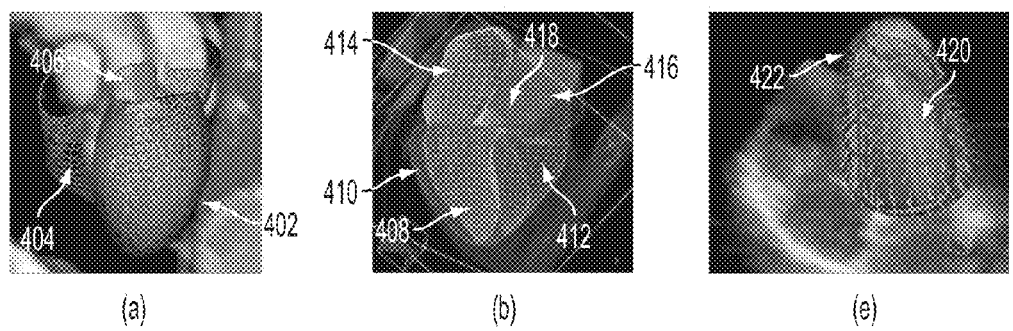
FIG. 4 illustrates examples of segmented patient-specific meshes of cardiac chambers.

The segmentation of the cardiac chambers results in a mesh for each segmented chamber generated for each frame of the 4D image data. FIG. 4 illustrates examples of segmented patient-specific meshes of cardiac chambers. As illustrated in FIG. 4, image (a) shows the left ventricle 402, right ventricle 404, and aortic root 406 segmented in an MR volume. Image (b) shows the left ventricle endocardium 408, left ventricle epicardium 410, right ventricle 412, left atrium 414, right atrium 416, and aortic root 418 segmented in a CT volume. Image (c) shows the left ventricle endocardium 420 and epicardium 422 segmented in an ultrasound volume.

Returning to FIG. 2, at step 208 the blood pool volume and arterial inflow are estimated over the cardiac cycle based on the segmented cardiac chambers. From the dynamic meshes of the ventricular chambers resulting from step 206, an estimate of blood pool volume is calculated. The blood pool volume is estimated at each time point based on the volume of the segmented ventricles in the corresponding frame of the 4D cardiac image data. In a possible implementation, the method for measuring left ventricle volume described in U.S. Pat. No. 8,098,918, which is incorporated herein by reference, can be used to calculate the blood pool volume in each frame. This results in volume curve with an estimated volume for each of a plurality of time points over at least one cardiac cycle. The temporal derivative of the volume curve provides the ventricular blood flow (negative during systole and positive during diastole) at each time point. The arterial inflow is equal to the opposite ventricular flow during systole, assuming no regurgitation. Accordingly, the arterial inflow is calculated at each time point based on the temporal derivative of the blood pool volume.

Figure 5:
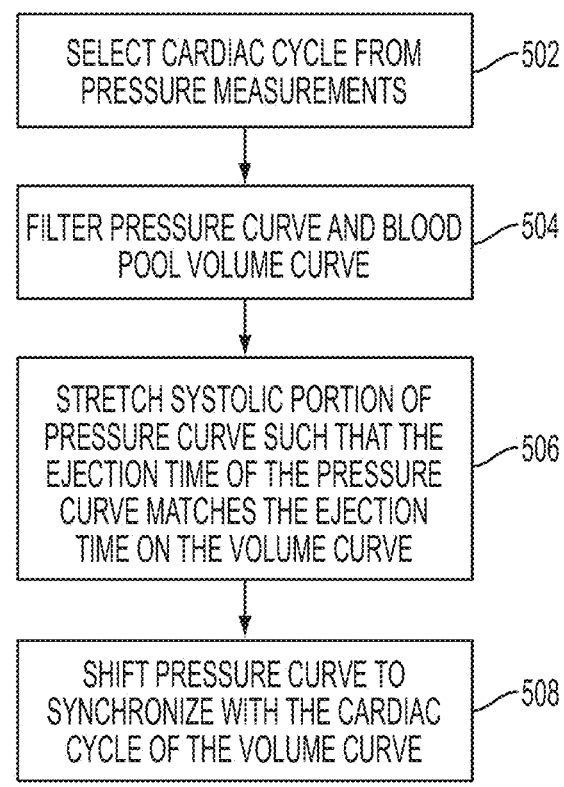
FIG. 5 illustrates a method for synchronizing the pressure measurement with the arterial inflow estimate according to an embodiment of the present invention.

At step 210, the pressure measurement, received at step 204, is adjusted to synchronize a cardiac cycle of the pressure measurement with a cardiac cycle of the arterial inflow estimate. FIG. 5 illustrates a method for synchronizing the pressure measurement with the arterial inflow estimate according to an embodiment of the present invention. It is to be understood that the method of claim 5 can be used to implement step 210 of FIG. 2.

Referring to FIG. 5, at step 502, a cardiac cycle is selected from the pressure measurement. The pressure measurement is a measurement of the arterial and ventricular blood pressure over time, which will typically cover more than one cardiac cycle. One cardiac cycle is selected from the pressure measurement for synchronization with the arterial inflow estimate. According to a possible implementation, the cardiac cycle is selected by displaying the pressure measurement (e.g., on a display device of a computer) and receiving a user input (e.g., via a mouse or other user input device) indicating manual selection of a cardiac cycle in the pressure measurement. In another possible implementation, the cardiac cycle can be selected from the pressure measurement automatically. The selection of a cardiac cycle in the pressure measurement results in a pressure curve including the arterial and ventricular pressure over the selected cardiac cycle.

Figure 6:
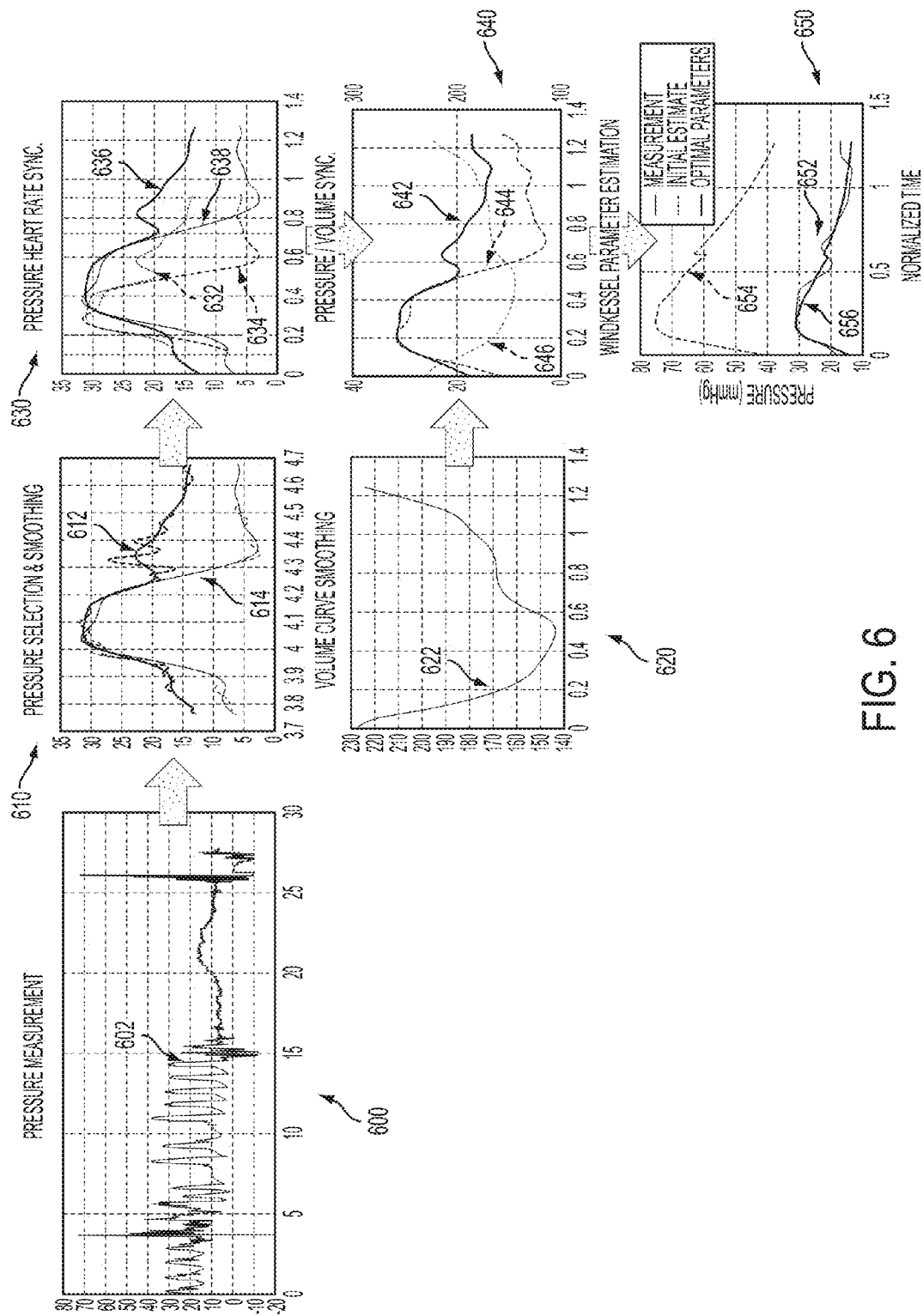
FIG. 6 illustrates synchronizing the pressure measurement and arterial inflow estimate and estimating arterial compliance and resistance according to an embodiment of the present invention.

At step 504, the pressure curve and the blood pool volume curve estimated from the segmented ventricular chambers are filtered. In an advantageous embodiment, the arterial and ventricular pressure, as well as the blood pool volume curve, are smoothed by filtering the curves using a low-pass filter. However, the present invention is not limited to smoothing the curves using low-pass filter and other types of filtering may be performed. FIG. 6 illustrates synchronizing the pressure measurement and arterial inflow estimate and estimating arterial compliance and resistance according to an embodiment of the present invention. As shown in FIG. 6, image 600 shows the pressure measurement 602 and image 610 shows the arterial and ventricular pressure curves 612 and 614 resulting from selecting a cardiac cycle from the pressure measurement 602 and smoothing the resulting pressure curve. Image 620 of FIG. 6 shows the smoothed volume curve 622.

Steps 506 and 508 are performed to automatically adjust the pressure curve to match the heart rate at the 4D cardiac image data acquisition so that the pressure curve will be synchronized with the arterial inflow estimate. As simple temporal scaling would not be physiologically coherent, a rule-based algorithm is applied to adjust the pressure curve. At step 506, the systolic portion of the pressure curve is stretched such that the ejection time observed on the pressure curve is equal to the ejection time measured on the volume curve. The ejection time on the pressure curve is the time during which the ventricular pressure is higher than or equal to the arterial pressure. The ejection time on the blood pool volume curve is the time during which the ventricular flow is negative. As described above, the ventricular blood flow is the temporal derivative of the blood pool volume. Accordingly, the ejection time on the blood pool volume curve is the time during which the derivative or slope of the volume curve is negative. Image 630 of FIG. 6 shows the synchronization of the pressure curve with the heart rate during image acquisition by stretching the systolic portion of the pressure curve such that the ejection time of the pressure curve matches the ejection time of the blood pool volume curve. As shown in image 630, curves 632 and 634 are the arterial and ventricular pressure curves, respectively, prior to the adjustment and curves 636 and 638 are the adjusted arterial and ventricular pressure curves, respectively, that have been adjusted by stretching the systolic portion such that the ejection time of the curves 636 and 638 is equal to the ejection time measured in the blood pool volume curve 622.

At step 508, the pressure curve is shifted to synchronize the pressure curve with the cardiac cycle of the blood pool volume curve. Once the systolic portion of the pressure curve is stretched such that the ejection time of the pressure curve is equal to the ejection time of the volume curve, the remaining portion of the pressure curve can be adjusted such that the total time for the cardiac cycle is equal to the total time of the cardiac cycle in the volume curve. The pressure curve is then shifted so that it is aligned in time with the blood pool volume curve. Image 640 of FIG. 6 shows the arterial and ventricular pressure curve 642 and 644, respectively, synchronized with the blood pool volume curve 646. It is to be understood that once the pressure curve is synchronized with the volume curve, the pressure curve is also synchronized with the arterial inflow estimate since the arterial inflow estimate is calculated based on the temporal derivative of the volume curve. The method of FIG. 5 may be repeated for a number of cardiac cycles of the pressure measurement to generate multiple synchronized pressure samples.

Figure 7:
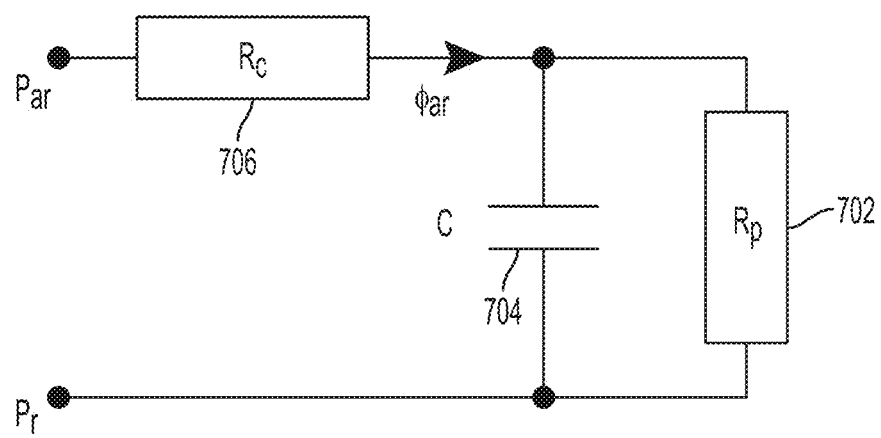
FIG. 7 illustrates a 3-element Windkessel model.

Returning to FIG. 2, at step 212, the arterial compliance and resistance are estimated based on the synchronized pressure curve and arterial inflow estimate using a Windkessel model. According to an advantageous embodiment, the arterial pressure is modeled using a 3-element Windkessel model, which takes as input the arterial flow and returns the pressure with the artery at every time step of a simulation. It is to be understood that the present invention is not limited to a 3-element Windkessel model, but could be implemented similarly with a 2- or 4-element model as well. The Windkessel model is derived from electrical circuit analogies where the blood flow is the current and the arterial pressure is the voltage. FIG. 7 illustrates a 3-element Windkessel model. As shown in FIG. 7, the first element of the model is a peripheral resistance $R_p$ 702, which accounts for the distal resistance of the circulatory system mainly due to the small vessels. The compliance C 704 accounts for the elasticity of the arterial walls, whereas the characteristic resistance $R_c$ 706 accounts for the blood mass and for the compliance of the artery proximal to the valves. These parameters ($R_p$, C, and $R_c$) are estimated based on the synchronized pressure curve and arterial inflow estimate.

Let $\Phi_{ar}(t)$ be the arterial inflow at time t, defined as the opposite of the ventricular flow, $p_{ar}(t)$ be the arterial pressure at time t, and $p_r$ be a constant low pressure of reference (typically the pressure of the remote venous system). $p_r$ is typically set to be between 0 and 5 mm Hg and in a possible implementation $p_r=0$. When blood flows into the arteries ($\Phi_{ar}(t)>0$) during ejection, the 3-element Windkessel model can be expressed as:

$$\frac{d p_{ar}(t)}{dt} = R_c \frac{d\Phi_{ar}(t)}{dt} + \left(1 + \frac{R_c}{R_p}\right)\frac{\Phi_{ar}(t)}{C} - \frac{p_{ar}(t) - p_r}{R_p C}$$

When the valves are closed, the blood flow is stopped ($\Phi_{ar}(t)=0$), and the 3-element Windkessel model can be expressed as:

$$\frac{d p_{ar}(t)}{dt} = -\frac{p_{ar}(t) - p_r}{R_p C}$$

These equations can be integrated using first (or higher) order implicit or stable explicit schemes.

Once the pressure curve is synchronized with the arterial inflow estimate, the Windkessel model is used to calculate pressure for a plurality of time steps based on the arterial inflow estimate at each time step. The calculated pressure values are compared to the pressure values of the synchronized pressure curve and the parameters of the Windkessel model ($R_p$, C, and $R_c$) are calculated automatically using an optimization procedure is used to minimize a cost function.

The parameters of the Windkessel model can be initialized with preset default values, such as mean population wide arterial resistance and compliance values. According to an advantageous embodiment, the cost function used optimize the Windkessel parameters is:

$$\min_{R_c, R_p, C, p_0} \left\{ (\min(p_m) - \min(p_c))^2 + (\max(p_m)) - (\max(p_c))^2 + \frac{1}{N}\sum_{i=1}^{N}(p_m[i] - p_c[i])^2 \right\}$$

where $p_m$ and $p_c$ are vectors containing the time-sequence of measured and computed arterial pressure, respectively, $p_0$ is an initial arterial pressure value for the Windkessel model, and N is a number of pressure samples. According to a possible implementation, the simplex method can be used to minimize the cost function and estimate the optimal Windkessel parameters. For increased robustness, the cost function is duplicated over N cycles and the forward model calculated for all of these cycles. The cost function is evaluated only at the latest cycle. The simplex method is used to estimate all of the parameters but the initial pressure $p_0$. The initial pressure $p_0$ is obtained automatically from the computed pressure curve over several cycles, such that the first computed pressure cycle is close to steady state. Image 650 of FIG. 6 shows optimization of the Windkessel parameters using the calculated and measured pressure values. As shown in image 650, curve 652 is the measured arterial pressure curve that has been synchronized with the arterial inflow estimate, curve 654 is an initial estimate of the arterial pressure using the Windkessel model, and curve 656 is the calculated arterial pressure using the Windkessel parameter with optimal parameters.

Returning to FIG. 2, at step 214, the estimated arterial resistance and compliance are output. In particular, estimated values for the arterial resistance and compliance are determined in step 212 and these values can be output by displaying the estimated arterial resistance and compliance values, such as on a display device of computer system. The estimated arterial resistance and compliance values can also be output by storing these values on a memory or storage of a computer system or in a central database.

The methods described above utilize machine-learning techniques to estimate the arterial parameters and their uncertainty. The model being fast enough, a large database can be constructed by combining forward simulations and pairs of arterial parameters and patient data. A regression function can then be trained and used to estimate arterial parameters for new, unseen datasets. The database can further be employed to evaluate the uncertainty on the estimated parameters.

As described above, the pressure measurement of a patient is synchronized to and arterial inflow estimate obtained from medical image data of the patient. In another possible embodiment, the data synchronization can be performed using a lumped heart model for more realistic heart-rate synchronization. The lumped heart model is personalized from the observed cardiac parameters (ejection fraction, stroke volume) using the same approach as described above.

Figure 8:
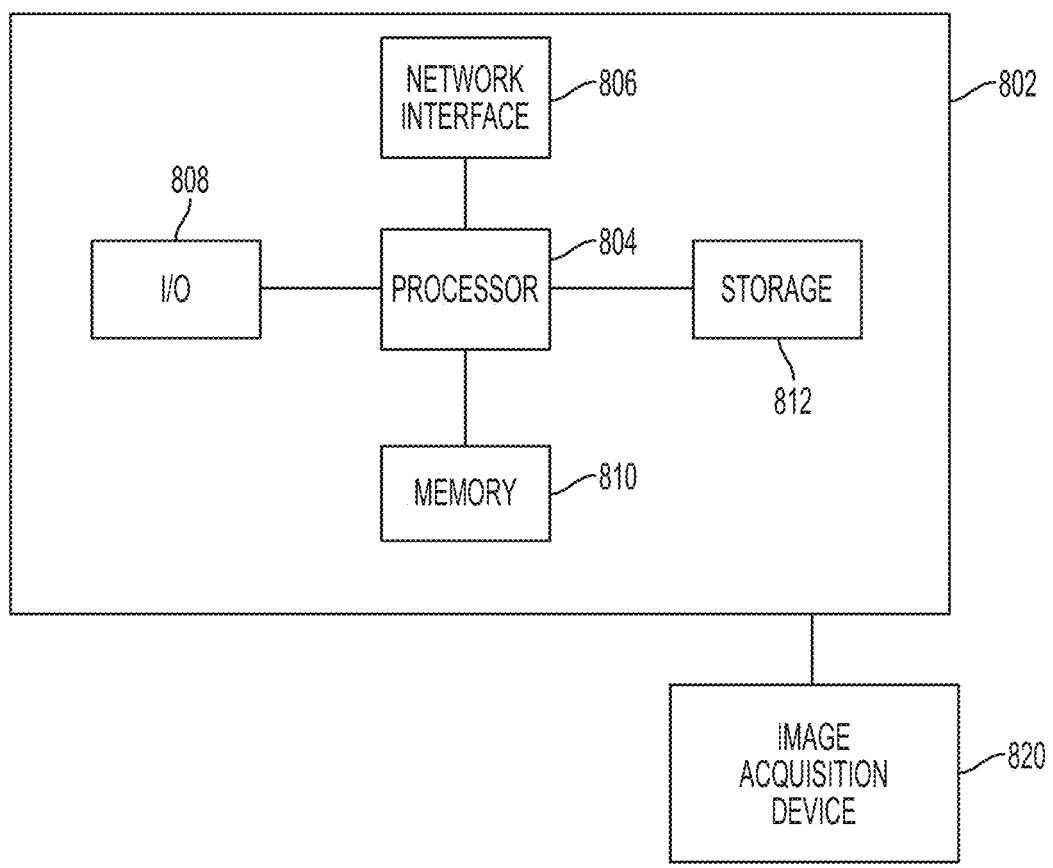
FIG. 8 is a high-level block diagram of a computer capable of implementing the present invention.

The above-described methods for estimating arterial compliance and resistance can be implemented on a computer using well-known computer processors, memory units, storage devices, computer software, and other components. A high-level block diagram of such a computer is illustrated in FIG. 8. Computer 802 contains a processor 804, which controls the overall operation of the computer 802 by executing computer program instructions which define such operation. The computer program instructions may be stored in a storage device 812 (e.g., magnetic disk) and loaded into memory 810 when execution of the computer program instructions is desired. Thus, the steps of the methods of FIGS. 1, 2, and 5 may be defined by the computer program instructions stored in the memory 810 and/or storage 812 and controlled by the processor 804 executing the computer program instructions. An image acquisition device 820, such as a CT scanning device, C-arm image acquisition device, MR scanning device, Ultrasound device, etc., can be connected to the computer 802 to input image data to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.). Such input/output devices 808 may be used in conjunction with a set of computer programs as an annotation tool to annotate volumes received from the image acquisition device 820. One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method of estimating arterial compliance and resistance of a patient, comprising:
   determining an arterial inflow estimate over a plurality of time points based on medical image data of a patient;
   receiving an arterial pressure measurement of the patient;
   synchronizing at least one cardiac cycle of the arterial pressure measurement with at least one cardiac cycle of the arterial inflow estimate; and
   estimating arterial compliance and resistance of the patient based on the arterial inflow estimate and the synchronized arterial pressure measurement.

2. The method of claim 1, wherein the medical image data comprises 4D medical image data and determining an arterial inflow estimate over a plurality of time points based on medical image data of a patient comprises:
   segmenting one or more cardiac chambers in each of a plurality of frames of the 4D medical image data;
   estimating a blood pool volume in each of the plurality of frames of the 4D medical image data based on the segmented one or more cardiac chambers; and
   estimating arterial inflow at each of the plurality of time points based on a temporal derivative of the blood pool volume at a respective frame corresponding to each of the plurality of time points.

3. The method of claim 2, wherein segmenting one or more cardiac chambers in each of a plurality of frames of the 4D medical image data comprises:
   segmenting a left ventricle and a right ventricle in each of the plurality of frames of the 4D medical image data.

4. The method of claim 2, wherein estimating arterial inflow at each of the plurality of time points based on a temporal derivative of the blood pool volume at a respective frame corresponding to each of the plurality of time points comprises:
   estimating a ventricular blood flow at each of the plurality of time points by calculating the temporal derivative of the blood pool volume at the respective frame corresponding to each of the plurality of time points; and
   estimating the arterial inflow at each of the plurality of time points as equal to and opposite the ventricular blood flow at each of the plurality of time points.

5. The method of claim 2, wherein synchronizing at least one cardiac cycle of the arterial pressure measurement with at least one cardiac cycle of the arterial inflow estimate comprises:
   selecting a cardiac cycle from the arterial pressure measurement, resulting in a pressure curve for the selected cardiac cycle;
   stretching a systolic portion of the pressure curve such that an ejection time in the pressure curve is equal to an ejection time in a volume curve resulting from estimating the blood pool volume in each of the plurality of frames in the 4D medical image data; and
   shifting the pressure curve to synchronize the pressure curve with the volume curve.

6. The method of claim 5, wherein synchronizing at least one cardiac cycle of the arterial pressure measurement with at least one cardiac cycle of the arterial inflow estimate further comprises:
   filtering the pressure curve and the volume curve prior to stretching the systolic portion of the pressure curve.

7. The method of claim 5, wherein shifting the pressure curve to synchronize the pressure curve with the volume curve comprises:
   adjusting a remaining portion of the pressure curve other than the systolic portion such that a total time of the cardiac cycle for the pressure curve is equal to a total time of a cardiac cycle for the volume curve; and
   aligning the pressure curve with the volume curve in time.

8. The method of claim 1, wherein synchronizing at least one cardiac cycle of the arterial pressure measurement with at least one cardiac cycle of the arterial inflow estimate comprises:
   adjusting the at least one cardiac cycle of the arterial pressure measurement to match a heart rate of the patient during acquisition of the medical image data.

9. The method of claim 1, wherein estimating arterial compliance and resistance of the patient based on the arterial inflow estimate and the synchronized arterial pressure measurement comprises:
   estimating arterial compliance and resistance of the patient based on the arterial inflow estimate and the synchronized arterial pressure measurement using a Windkessel model.

10. The method of claim 9, wherein estimating arterial compliance and resistance of the patient based on the arterial inflow estimate and the synchronized arterial pressure measurement using a Windkessel model comprises:
calculating arterial pressure over the plurality of time points based on the arterial inflow estimate over the plurality of time points using the Windkessel model to represent an artery; and
estimating compliance and resistance parameters of the Windkessel model to minimize a cost function that compares the arterial pressure calculated using the Windkessel model and the synchronized arterial pressure measurement.

11. The method of claim 1, wherein the medical image data comprises flow images and determining an arterial inflow estimate over a plurality of time points based on medical image data of a patient comprises:
measuring arterial inflow over the plurality of time points in the flow images.

12. An apparatus for estimating arterial compliance and resistance of a patient, comprising:
means for determining an arterial inflow estimate over a plurality of time points based on medical image data of a patient;
means for receiving an arterial pressure measurement of the patient;
means for synchronizing at least one cardiac cycle of the arterial pressure measurement with at least one cardiac cycle of the arterial inflow estimate; and
means for estimating arterial compliance and resistance of the patient based on the arterial inflow estimate and the synchronized arterial pressure measurement.

13. The apparatus of claim 12, wherein the medical image data comprises 4D medical image data and the means for determining an arterial inflow estimate over a plurality of time points based on medical image data of a patient comprises:
means for segmenting one or more cardiac chambers in each of a plurality of frames of the 4D medical image data;
means for estimating a blood pool volume in each of the plurality of frames of the 4D medical image data based on the segmented one or more cardiac chambers; and
means for estimating arterial inflow at each of the plurality of time points based on a temporal derivative of the blood pool volume at a respective frame corresponding to each of the plurality of time points.

14. The apparatus of claim 13, wherein the means for synchronizing at least one cardiac cycle of the arterial pressure measurement with at least one cardiac cycle of the arterial inflow estimate comprises:
means for selecting a cardiac cycle from the arterial pressure measurement, resulting in a pressure curve for the selected cardiac cycle;
means for stretching a systolic portion of the pressure curve such that an ejection time in the pressure curve is equal to an ejection time in a volume curve resulting from estimating the blood pool volume in each of the plurality of frames in the 4D medical image data; and
means for shifting the pressure curve to synchronize the pressure curve with the volume curve.

15. The apparatus of claim 14, wherein the means for synchronizing at least one cardiac cycle of the arterial pressure measurement with at least one cardiac cycle of the arterial inflow estimate further comprises:
means for filtering the pressure curve and the volume curve prior to stretching the systolic portion of the pressure curve.

16. The apparatus of claim 14, wherein the means for shifting the pressure curve to synchronize the pressure curve with the volume curve comprises:
means for adjusting a remaining portion of the pressure curve other than the systolic portion such that a total time of the cardiac cycle for the pressure curve is equal to a total time of a cardiac cycle for the volume curve; and
means for aligning the pressure curve with the volume curve in time.

17. The apparatus of claim 12, wherein the means for synchronizing at least one cardiac cycle of the arterial pressure measurement with at least one cardiac cycle of the arterial inflow estimate comprises:
means for adjusting the at least one cardiac cycle of the arterial pressure measurement to match a heart rate of the patient during acquisition of the medical image data.

18. The apparatus of claim 12, wherein the means for estimating arterial compliance and resistance of the patient based on the arterial inflow estimate and the synchronized arterial pressure measurement comprises:
means for estimating arterial compliance and resistance of the patient based on the arterial inflow estimate and the synchronized arterial pressure measurement using a Windkessel model.

19. The apparatus of claim 18, wherein the means for estimating arterial compliance and resistance of the patient based on the arterial inflow estimate and the synchronized arterial pressure measurement using a Windkessel model comprises:
means for calculating arterial pressure over the plurality of time points based on the arterial inflow estimate over the plurality of time points using the Windkessel model to represent an artery; and
means for estimating compliance and resistance parameters of the Windkessel model to minimize a cost function that compares the arterial pressure calculated using the Windkessel model and the synchronized arterial pressure measurement.

20. A non-transitory computer readable medium encoded with computer program instructions for estimating arterial compliance and resistance of a patient, the computer program instructions when executed by a processor cause the processor to perform operations comprising:
determining an arterial inflow estimate over a plurality of time points based on medical image data of a patient;
receiving an arterial pressure measurement of the patient;
synchronizing at least one cardiac cycle of the arterial pressure measurement with at least one cardiac cycle of the arterial inflow estimate; and
estimating arterial compliance and resistance of the patient based on the arterial inflow estimate and the synchronized arterial pressure measurement.

21. The non-transitory computer readable medium of claim 20, wherein the medical image data comprises 4D medical image data and determining an arterial inflow estimate over a plurality of time points based on medical image data of a patient comprises:
segmenting one or more cardiac chambers in each of a plurality of frames of the 4D medical image data;
estimating a blood pool volume in each of the plurality of frames of the 4D medical image data based on the segmented one or more cardiac chambers; and
estimating arterial inflow at each of the plurality of time points based on a temporal derivative of the blood pool volume at a respective frame corresponding to each of the plurality of time points.

22. The non-transitory computer readable medium of claim 21, wherein estimating arterial inflow at each of the plurality of time points based on a temporal derivative of the blood pool volume at a respective frame corresponding to each of the plurality of time points comprises:

estimating a ventricular blood flow at each of the plurality of time points by calculating the temporal derivative of the blood pool volume at the respective frame corresponding to each of the plurality of time points; and estimating the arterial inflow at each of the plurality of time points as equal to and opposite the ventricular blood flow at each of the plurality of time points.

23. The non-transitory computer readable medium of claim 21, wherein synchronizing at least one cardiac cycle of the arterial pressure measurement with at least one cardiac cycle of the arterial inflow estimate comprises:

selecting a cardiac cycle from the arterial pressure measurement, resulting in a pressure curve for the selected cardiac cycle;

stretching a systolic portion of the pressure curve such that an ejection time in the pressure curve is equal to an ejection time in a volume curve resulting from estimating the blood pool volume in each of the plurality of frames in the 4D medical image data; and shifting the pressure curve to synchronize the pressure curve with the volume curve.

24. The non-transitory computer readable medium of claim 23, wherein synchronizing at least one cardiac cycle of the arterial pressure measurement with at least one cardiac cycle of the arterial inflow estimate further comprises:

filtering the pressure curve and the volume curve prior to stretching the systolic portion of the pressure curve.

25. The non-transitory computer readable medium of claim 23, wherein shifting the pressure curve to synchronize the pressure curve with the volume curve comprises:

adjusting a remaining portion of the pressure curve other than the systolic portion such that a total time of the cardiac cycle for the pressure curve is equal to a total time of a cardiac cycle for the volume curve; and aligning the pressure curve with the volume curve in time.

26. The non-transitory computer readable medium of claim 20, wherein synchronizing at least one cardiac cycle of the arterial pressure measurement with at least one cardiac cycle of the arterial inflow estimate comprises:

adjusting the at least one cardiac cycle of the arterial pressure measurement to match a heart rate of the patient during acquisition of the medical image data.

27. The non-transitory computer readable medium of claim 20, wherein estimating arterial compliance and resistance of the patient based on the arterial inflow estimate and the synchronized arterial pressure measurement comprises:

estimating arterial compliance and resistance of the patient based on the arterial inflow estimate and the synchronized arterial pressure measurement using a Windkessel model.

28. The non-transitory computer readable medium of claim 27, wherein estimating arterial compliance and resistance of the patient based on the arterial inflow estimate and the synchronized arterial pressure measurement using a Windkessel model comprises:

calculating arterial pressure over the plurality of time points based on the arterial inflow estimate over the plurality of time points using the Windkessel model to represent an artery; and estimating compliance and resistance parameters of the Windkessel model to minimize a cost function that compares the arterial pressure calculated using the Windkessel model and the synchronized arterial pressure measurement.

\* \* \* \* \*